United States Patent [19]

Papenfuhs et al.

[11] Patent Number: 5,227,545
[45] Date of Patent: Jul. 13, 1993

[54] PROCESS FOR THE PREPARATION OF 2,4-DICHLOROFLUOROBENZENE

[75] Inventors: Theodor Papenfuhs; Georg Folz, both of Frankfurt am Main; Ralf Pfirmann, Griesheim, all of Fed. Rep. of Germany

[73] Assignee: Hoechst Aktiengesellschaft, Frankfurt am Main, Fed. Rep. of Germany

[21] Appl. No.: 958,287

[22] Filed: Oct. 8, 1992

[30] Foreign Application Priority Data

Oct. 11, 1991 [DE] Fed. Rep. of Germany ....... 4133689

[51] Int. Cl.$^5$ .................... C07C 25/13; C07C 17/10
[52] U.S. Cl. ..................... 570/147; 570/143
[58] Field of Search .................. 570/147, 143

[56] References Cited

U.S. PATENT DOCUMENTS 3,277,192 10/1966 Fielding ............... 570/147
5,157,169 10/1992 Patton ................ 570/147

FOREIGN PATENT DOCUMENTS 0307481 3/1989 European Pat. Off. .
0355719 2/1990 European Pat. Off. .

Primary Examiner—Alan Siegel

[57] ABSTRACT

Process for the preparation of 2,4-dichlorofluorobenzene in high yield and purity without intermediate separation of the isomers formed,(1) by nitrating 1 mol of fluorobenzene to give nitrofluorobenzene using a mixture comprising 35 to 65 parts by weight of 50 to 90% strength sulfuric acid and 35 to 65 parts by weight of a nitrating acid comprising 35 to 55 parts by weight of 95 to 98% strength sulfuric acid and 45 to 65 parts by weight of 96 to 98% strength nitric acid, with the proviso that 0.8 to 2.0 equivalents of the nitrating agent $NO_2^+$ are used per mol of fluorobenzene, at 20° to 90° C., (2) allowing 25 g to 150 g of chlorine, in the presence of a ring chlorinating catalyst, to act on each 100 g of the crude nitrofluorobenzene mixture obtained, at 20° to 100° C., and (3) allowing about 18 g to about 203 g of chlorine or equivalent amounts of a chlorine releasing agent to act on each 100 g of the crude chlorofluoronitrobenzene mixture obtained, after removal of the ring chlorinating catalyst, at 110° to 220° C., and isolating the 2,4-dichlorofluorobenzene.

19 Claims, No Drawings

PROCESS FOR THE PREPARATION OF 2,4-DICHLOROFLUOROBENZENE

The present invention relates to a process for the preparation of 2,4-dichlorofluorobenzene in high yield and purity in a three-stage process, in which only the end product is purified by fractionation or melt crystallization, but each of the intermediate is further processed in the crude form. In this case, separation of the isomers of the intermediates, which can be expensive, is avoided as being unnecessary because the isomers which are produced are converted into the same end product. The desired end product contains only 2% of 2,6-dichlorofluorobenzene as an impurity before fractionation.

2,4-Dichlorofluorobenzene, which may be prepared economically according to the invention, is a valuable intermediate in the preparation of antibacterial agents of the quinolonecarboxylic acid series. It can be converted by acylation and subsequent oxidation (DE 3435392; DE 3925036; EP 411252) into 2,4-dichloro-5-fluorobenzoic acid, which may be converted into quinolonecarboxylic acid derivatives by processes disclosed in the literature. (DE 3702393; DE 3615767; DE 3601567; DE 3600891; DE 3522406; DE 3517535; DE 3641312). 2,4-Dichloro-5-fluoroacetophenone, which may be obtained by acylation, may also be used directly as the basis for synthesizing antibacterially active compounds (EP 131839). Also possible is the bromination of 2,4-dichlorofluorobenzene and subsequent bromine-cyanide exchange and fluorination to give 2-chloro-4,5-difluorobenzonitrile, which is converted into 2-chloro-4,5-difluorobenzoic acid (EP 433124) and represents a more favourable precursor for quinolonecarboxylic acid derivatives (EP 342849; EP 321191; EP 303291). 2,4,5-trifluorobenzoic acid may also be prepared in this way and this may be converted into antibacterially active compounds in the same way (J. P. Sanchez, J. M. Domagala, S. E. Hagen, C. L. Heifetz, M. P. Hutt, J. B. Nichols, A. K. Trehan, J. Med. Chem. 31 (1988), 983-991; EP 227088; DE 3600891; DE 3420743; JP 60072885; EP 191185). Acylation of 2,4-dichlorofluorobenzene using phosgene to give 2,4-dichloro-5-fluorobenzoyl chloride is also possible (JP 01226851), and this may then be converted either into 2,4-dichloro-5-fluorobenzoic acid by indirect hydrolysis (JP 01226851, loc. cit.) or into 2,4,5-trifluorobenzoic acid by a chlorine-fluorine exchange reaction and alkaline hydrolysis (DE 3420796).

Hitherto, 2,4-dichlorofluorobenzene has been prepared by a Sandmeyer reaction using 3-chloro-4-fluoroaniline (Houben-Weyl-Müller, Methods in Organic Chemistry, vol. 5/3 (1963), 846-853). However, Sandmeyer reactions are always accompanied by low space-time yields and high contamination of waste water. 3-Chloro-4-fluoroaniline has been prepared from 3-chloro-4-fluoronitrobenzene by reduction, this being produced in the process according to the invention as an intermediate which does not need purifying and which may be prepared either by chlorination of isomerically pure 4-fluoronitrobenzene (EP 307481, loc. cit.; van de Lande, Rec. Trav. Chim. Pays-Bas, 51 (1932), 98-101; Rinkes, Chemisches Zentralblatt (1914/II), 1432) or by a halex (chlorine, fluorine) reaction from 3,4-dichloronitrobenzene (DE 2938939; U.S. Pat. No. 4,229,365), which may be readily obtained by nitration of o-dichlorobenzene and is already available industrially in large amounts.

It has now been found that 2,4-dichlorofluorobenzene may be prepared in high yields and high purity in a three-stage process without intermediate separation of the isomers formed, by (1) nitrating 1 mol of fluorobenzene to give nitrofluorobenzene using a mixture comprising about 35 to about 65 parts by weight of about 50 to 90% strength, preferably about 65 to about 75% strength, sulfuric acid, 35 to about 65 parts by weight of nitrating acid comprising about 35 to about 55 parts by weight of about 95 to about 98% strength sulfuric acid and about 45 to about 65 parts by weight of about 96 to about 98% strength nitric acid, with the proviso that about 0.8 to about 2.0 equivalents, preferably about 0.9 to 1.2 equivalents, of nitrating agent $NO_2^+$ are used per mole of fluorobenzene, at temperatures of about 20° to about 90° C., preferably of about 50° to about 70° C., optionally in the presence of a solvent or diluent, (2) allowing about 25 g to about 150 g, preferably about 27 g to about 50 g, particularly preferably about 27 to about 33 g of chlorine, or equivalent amounts of a chlorine releasing agent, to act on each 100 g of the crude nitrofluorobenzene mixture obtained in this way, in the presence of a ring chlorinating catalyst, optionally in the presence of a diluent, at temperatures of about 20° to about 100° C., preferably of about 50° to about 70° C., and (3) allowing about 18 g to about 203 g, preferably about 22 g to about 81.2 g, particularly preferably about 22 g to about 40,6 g, of chlorine or equivalent amounts of a chlorine releasing agent to act on each 100 g of the crude chlorofluoronitrobenzene mixture obtained (denitrating chlorination), after removal of the ring chlorinating catalyst, optionally in the presence of a diluent and optionally in the presence of a dehydrating agent and/or a fluoride scavenger, at temperatures of about 110° C. to about 220° C., preferably of about 175° C. to about 190° C., and then isolating the 2,4-dichlorofluorobenzene by fractional distillation or melt crystallization.

The following gives more details on the individual process stages.

On the first stage (nitration of fluorobenzene): it is expedient to nitrate the fluorobenzene in an emulsion comprising the sulfuric acid and nitrating acid mentioned and any solvent or diluent present. The solvent or diluent to be used may be, for example, nitrobenzene, chlorinated nitrobenzenes or fluorinated nitrobenzenes, for example a crude nitrofluorobenzene mixture, as is produced for example in the process according to the invention, dichloromethane, trichloromethane, tetrachloromethane, 1,2-dichloroethane and lower paraffins such as for example n-hexane, octane or similar. The nitration may be performed either discontinuously (batchwise) or continuously. When working continuously, the nitrating acid is preferably used in amounts such that about 1.0 to about 1.1 equivalents of the nitrating agent ($NO_2^+$), are used per mol of fluorobenzene.

In addition, it is expedient to work in a cascade preferably comprising 3 to 5 tanks.

In the case of discontinuous (batchwise) nitration, unreacted fluorobenzene may either be scavenged by relatively high excesses of nitrating acid or separated and returned to the process after distillation of unreacted material. The overall yields in the first stage are more than 95% when working batchwise, and more than 99% when working continuously, relative to the fluorobenzene used.

In contrast to the process described in EP 307481, the isomers which are produced here are not separated, which would require considerable effort in fractionation due to the small difference in boiling points, but are subjected to the second stage as a mixture (chlorination using chlorine or a chlorine releasing agent). Suitable chlorine releasing agents are for example antimony pentachloride, iodine trichloride, sulfur dichloride, disulfur dichloride or manganese tetrachloride or mixtures thereof.

The chlorination (in the second stage of the process according to the invention) is performed in the presence of a ring chlorinating catalyst, such as iron, iron(II) chloride, iron(III) chloride, iodine, iodine trichloride, iodine pentachloride, antimony trichloride, antimony pentachloride or aluminum(III) chloride or a mixture thereof, preferably in the presence of iron(III) chloride. The chlorination in the second stage of the reaction is preferably performed in the absence of a diluent. However, it may also be performed in the presence of an inert organic solvent such as, for example, tetrachloromethane, chloroform, 1,2-dichloroethane, oleum, sulfuric acid or chlorosulfonic acid. The product mixture obtained in the second stage comprises about 87% of 3-chloro-4-fluoronitrobenzene, about 11% of 2-fluoro-5-chloronitrobenzene and about 2% of 2-fluoro-3-chloronitrobenzene. Other components, such as 2,4-dinitrofluorobenzene which has not reacted further during chlorination in the second stage, are present in amounts of less than 0.1% of the total. In this stage also (the total yields of mixture are more than 90%), the yields are more than 95%. Separation of the compounds which are obtained does not take place. Removal of the ring chlorinating catalyst takes place, after prior removal of any diluent present by phase separation and washing or by distillation, by washing the organic phase several times with water and/or dilute sodium hydroxide solution. It is also possible to separate the product mixture which is produced in the second stage from the catalyst remaining at the bottom by simple distillation. The boiling range of the product mixture is about 75° to 100° C. at 4 mbar.

In the event that pure compounds are used, denitrating chlorination has been disclosed in several examples in the literature, also for 2,4-dichlorofluorobenzene as product (N. N. Voroshtsov, G. G. Yakobson, N. I. Krizhechkovskaya, A. I. D'yachenko, I. V. Shikanova, Zh. Obshch. Khim. 31(4), 1222-1226 (1961), CA 55 (1961), 24605i; N. N. Voroshtsov, G. G. Yakobson, N. I. Krizhechkovskaya, Khim. Nauka i Prom. 3 (1958), 404–405, CA 52 (1958) 19987h; V. A. Solenko, N. N. Voroshtsov, G. G. Yakobson, Izv. Sibirsk. Otd. Akad. Nauk SSSR (1962/10), 87–90, CA 59, 1507b; L. C. Kun, K. G. Lo, P. G. Pil, C. J. Pung, Hwahak Kwa Hwahak Kongop (1972/5), 251–253, CA 79 (1973), 31599n; EP 163230; EP 355719; EP 180057; EP 150587). However, it was surprising that the crude mixture unpurified in the previous two stages entered so smoothly into reaction and could be converted continuously, which is not always possible in the presence of impurities.

Replacement of the nitro groups by chlorine in the third reaction stage is performed at temperatures of about 110° to about 200° C. A temperature of 175° to 190° C. is preferred at the bottom of the column because then 2,4-dichlorofluorobenzene may be distilled off evenly as the crude product. The preferred amounts of chlorine to be used when working continuously are about 50 to about 200 ml/g·h. However, this last stage may also be performed discontinuously (batchwise) by introducing chlorine in a sub-stoichiometric amount (about 20 to about 30%) and subsequently distilling off the lower boiling product. It is expedient to add dehydrating agents and/or fluoride scavengers to the chlorinating bottom in order to prevent corrosion by hydrogen fluoride, which may be intensified by the use of the crude mixtures according to the invention as compared with the pure compounds. Calcium salts, such as calcium chloride, calcium sulfate or calcium hydroxide, and silicon dioxide are preferred as fluoride scavengers. Dehydrating agents which may be used are phosphorus pentoxide or phosphorus pentachloride.

The overall yields of 2,4-dichlorofluorobenzene, relative to the fluorobenzene used, are 85 to 90%; the purity of the distilled crude product is greater than 97%. 2,6-Dichlorofluorobenzene which is also produced in amounts of about 2% (b. pt. 179° C.) and other minor components (see process description) may be separated out during fractionation as components which boil off after the desired product (b. pt. 171° C.) (atmospheric pressure). However, fractionation may also be performed under a vacuum. The reduced difference in boiling points must then be compensated for by the use of a column with a larger number of separating steps. It is also possible to separate the isomers by melt crystallization, because the main impurity has a much higher solidification point, 41° C., than the desired product (below −25° C.).

The following example serves to explain the process without representing a limitation.

EXAMPLE a) Nitration of fluorobenzene

Fluorobenzene (288 g/h, 3 mol), in an emulsion with nitric acid (96%, 204 g/h) and sulfuric acid (98%, 175 g/h), is nitrated in a cascade comprising 3 stirred apparatuses, at temperatures of 45° to 50° C. (1st tank), 50° to 55° C. (2nd tank) and 55° to 60° C. (3rd tank). The mean residence time is set at about 3 hours. The emulsion is maintained by adding 72% strength sulfuric acid at 392 g/h. 1057 g of nitrating mixture may be removed per hour, this containing 423 g of a mixture of nitrofluorobenzene isomers besides about 625 g of 72% strength sulfuric acid and about 9 g of nitric acid. The upper organic phase is washed with 250 g of water, 250 g of 2.5% strength sodium hydrogen carbonate solution and again with 250 g of water until neutral and the lower phase of residual acid may be recycled. 420 g (318 ml) of organic phase (nitrofluorobenzene, 99.2% relative to fluorobenzene) which contains 0.3% m-nitrofluorobenzene, 85.7% p-nitrofluorobenzene and 0.4% 2,4-dinitrofluorobenzene remains. The mixture is used in this form in the subsequent reaction.

If nitration is performed batchwise at temperatures between about 20° and about 80° C., preferably between about 50° and about 70° C., the same result is obtained if the excess of nitrating acid is chosen so that no fluorobenzene remains or, when a smaller excess is used, the unconverted fluorobenzene is removed from the nitrating mixture by simple distillation and recycled.

b) Chlorination of the crude nitrofluorobenzene mixture

The amount of crude nitrofluorobenzene mixture (420 g) which is obtained from stage a) is treated with 3 g of iron turnings. Then chlorine is introduced at 60° C. until nitrofluorobenzene can no longer be detected by GC (in general after 9 to 11 hours). The catalyst is removed by washing the organic phase with water (250 g) and 5% strength sodium hydroxide solution (250 g). 518 g of an organic mixture of chlorofluoronitrobenzenes, which is used in stage c) without further treatment, remains. The mixture contains 85 to 87% of 3-chloro-4-fluoronitrobenzene, 10 to 12% of 2-fluoro-5-chloronitrobenzene, 1 to 3% of 2-fluoro-3-chloronitrobenzene, less than 0.1% of 2,4-dinitrofluorobenzene and less than 0.3% of chlorination products from 3-fluoronitrobenzene, such as 2-chloro-5-fluoronitrobenzene, 3-chloro-5-fluoronitrobenzene, 3-fluoro-4-chloronitrobenzene and 2-chloro-3-fluoronitrobenzene; dichlorinated fractions are also estimated to be less than 0.3%.

If, instead of iron turnings, 5.5 g of iron(III) chloride or 3 g of antimony(V) chloride or 1 g of iodine trichloride or 6 g of aluminum trichloride or a mixture of these catalysts in appropriate molar amounts is used, essentially the same result is obtained. If chlorination is performed at 50° C. (70° C.), then the starting compound can no longer be detected after 15 (7 to 8) hours. The isomeric ratios are scarcely dependent on temperature in this range, but the yields fall by about 3% (70° C.) or 6% (90° C.) at elevated temperature. To be certain of complete separation from the residual catalysts, the crude product mixture may be distilled under vacuum (boiling range 75° to 100° C. at 4 mbar corresponding to 400 Pa).

c) Denitrating chlorination

The amount of crude mixture obtained from process stage b) (518 g) is heated to 180° C. A stream of chlorine gas is passed into the mixture at a rate of 7 l/h. After about 2 hours sufficient product has formed and this is distilled off (boiling range 165° to 175° C.) over a 40 cm column filled with glass coils. Material obtained from further batch ring chlorination batches (process stage b) is added at the rate at which the product mixture is removed (45 g/h) in order to ensure continuous operation. Thus, about 43 g/h of product mixture is recovered, along with a strongly acid aqueous phase and gases containing nitrogen oxides. After hourly separation of this phase, the organic phase is washed neutral with water (twice, 50 g) and 10% strength sodium hydroxide solution (50 g). The organic phase, which comprises about 97 to about 98% of 2,4-dichlorofluorobenzene, about 2% of 2,6-dichlorofluorobenzene and less than 0.2% of other minor components, such as 3,4- and 3,5-dichlorofluorobenzene, is then fractionated at atmospheric pressure over a 30-plate column. A preliminary fraction passes over first at 165° to 170° C. (temperature at the base, 180° to 185° C.). At 171° to 172° C., 2,4-dichlorofluorobenzene is obtained with a purity of more than 99.5%; higher purities may be achieved by removing a larger preliminary fraction or by fractionating at a higher rate of reflux. Following the desired product, 2,6-dichlorofluorobenzene passes over at 179° C., the mixed fractions obtained being recycled. The yield of 2,4-dichlorofluorobenzene from the denitrating chlorination stage is 89% relative to the crude mixture and 86.5% relative to the fluorobenzene used in the first process stage. In the bottom of the reaction vessel, a mixture of trichlorofluorobenzene isomers accumulates and this is removed after about 200 hours' continuous operating time. This takes place by fractionating the contents of the vessel, the distillation residue then being discarded. If 5 g of calcium chloride or 8 g of silicon dioxide are added, the same result is obtained, but material removal due to corrosion in the apparatus which is used can be greatly reduced.

Instead of fractionating the washed crude product, the impurities may be almost completely separated out by melt crystallization at about −15° C. The liquid phase is 2,4-dichlorofluorobenzene with a purity of more than 99.8%.

We claim:

1. A process for the preparation of 2,4-dichlorofluorobenzene in high yields and high purity in a three-stage process without intermediate separation of the isomers formed, wherein (1) 1 mol of fluorobenzene is nitrated to give nitrofluorobenzene using a mixture comprising about 35 to about 65 parts by weight of about 50 to about 90% strength sulfuric acid and about 35 to about 65 parts by weight of nitrating acid comprising about 35 to about 55 parts by weight of about 95 to about 98% strength sulfuric acid and about 45 to about 65 parts by weight of about 96 to about 98% strength nitric acid, with the proviso that about 0.8 to about 2.0 equivalents of nitrating agent $NO_2^+$ are used per mol of fluorobenzene, at temperatures of about 20° to about 90° C., optionally in the presence of a solvent or diluent, (2) about 25 g to about 150 g of chlorine, or equivalent amounts of a chlorine releasing agent, are allowed to act on each 100 g of the crude nitrofluorobenzene mixture obtained, in the presence of a ring chlorinating catalyst, optionally in the presence of a diluent, at temperatures of about 20° to about 100° C., and (3) about 18 g to about 203 g of chlorine or equivalent amounts of a chlorine releasing agent are allowed to act on each 100 g of the crude chlorofluoronitrobenzene mixture obtained (denitrating chlorination), after removal of the ring chlorinating catalyst, optionally in the presence of a diluent and optionally in the presence of a dehydrating agent and/or a fluoride scavenger, at temperatures of about 110° C. to about 220° C. and then the 2,4-dichlorofluorobenzene is isolated by fractional distillation or melt crystallization.

2. The process as claimed in claim 1, wherein the mixture used for nitrating comprising sulfuric acid and nitrating acid contains an about 65 to about 75% strength sulfuric acid.

3. The process as claimed in claim 1, wherein about 0.9 to about 1.2 equivalents of the nitrating agent $NO_2^+$ per mol of fluorobenzene are used with the nitrating acid used.

4. The process as claimed in claim 1, wherein nitration is carried out continuously or batchwise.

5. The process as claimed in claim 1, wherein in the case of continuous nitration, about 1.0 to about 1.1 equivalents of the nitrating agent $NO_2^+$ per mol of fluorobenzene are used with the nitrating acid used.

6. The process as claimed in claim 1, wherein nitration is carried out at temperatures of about 50° to about 70° C.

7. The process as claimed in claim 1, wherein nitration is carried out in the presence of nitrobenzene, chlorinated nitrobenzenes, fluorinated nitrobenzenes, a crude nitrofluorobenzene mixture such as is produced in the process according to the invention, dichloromethane, trichloromethane, tetrachloromethane, 1,2-dichloroethane or lower paraffins as solvent or diluent.

8. The process as claimed in claim 1, which, in the case of continuous nitration is carried out in a cascade comprising 3 to 5 tanks.

9. The process as claimed in claim 1, wherein chlorination of the crude nitrofluorobenzene mixture obtained on nitration is performed in the presence of iron, iron(II) chloride, iron(III) chloride, iodine, iodine trichloride, iodine pentachloride, antimony trichloride, antimony pentachloride or aluminum(III) chloride or mixtures thereof.

10. The process as claimed in claim 1, wherein about 27 g to about 50 g of chlorine or equivalent amounts of a chlorine releasing agent are allowed to act on each 100 g of the crude nitrofluorobenzene mixture obtained on nitration.

11. The process as claimed in claim 1, wherein about 27 to about 33 g of chlorine or equivalent amounts of a chlorine releasing agent are allowed to act on each 100 g of the crude nitrofluorobenzene mixture obtained on nitration.

12. The process as claimed in claim 1, wherein the chlorine or chlorine releasing agent is allowed to act on the crude nitrofluorobenzene mixture, obtained on nitration, at temperatures of about 50° to about 70° C.

13. The process as claimed in claim 1, wherein the crude nitrofluorobenzene mixture obtained on nitration is chlorinated in the presence of tetrachloromethane, 1,2-dichloroethane, chloroform, dichloromethane, chlorosulfonic acid, oleum or sulfuric acid.

14. The process as claimed in claim 1, wherein the denitrating chlorination is carried out at temperatures of about 175° to about 190° C.

15. The process as claimed in claim 1, wherein about 22 g to about 81.2 g of chlorine or equivalent amounts of a chlorine releasing agent are allowed to act on each 100 g of the crude chlorofluoronitrobenzene mixture obtained in the second stage.

16. The process as claimed in claim 1, wherein about 22 g to about 40.6 g of chlorine or equivalent amounts of a chlorine releasing agent are allowed to act on each 100 g of the crude chlorofluoronitrobenzene mixture obtained in the second stage.

17. The process as claimed in claim 1, wherein the denitrating chlorination is performed in the presence of phosphorus pentoxide or phosphorus pentachloride as dehydrating agent.

18. The process as claimed in claim 1, wherein the denitrating chlorination is performed in the presence of calcium chloride, calcium hydroxide, calcium sulfate or silicon dioxide as fluoride scavenger.

19. The process as claimed in claim 1, wherein the denitrating chlorination is performed continuously or batchwise.

* * * * *